(12) United States Patent
Bernardes et al.

(10) Patent No.: US 9,346,851 B2
(45) Date of Patent: May 24, 2016

(54) CHEMICAL MODIFICATION OF PROTEINS

(75) Inventors: Goncalo Bernardes, Oxford (GB);
Justin Chalker, Oxford (GB);
Benjamin Davis, Oxford (GB)

(73) Assignee: R.P. Scherer Technologies, LLC, Las Vegas, NV (US)

( * ) Notice: Subject to any disclaimer, the term of this patent is extended or adjusted under 35 U.S.C. 154(b) by 552 days.

(21) Appl. No.: 12/918,678

(22) PCT Filed: Jan. 23, 2009

(86) PCT No.: PCT/GB2009/000194
§ 371 (c)(1),
(2), (4) Date: Feb. 15, 2011

(87) PCT Pub. No.: WO2009/103941
PCT Pub. Date: Aug. 27, 2009

(65) Prior Publication Data
US 2011/0144304 A1 Jun. 16, 2011

(30) Foreign Application Priority Data
Feb. 22, 2008 (GB) .................................. 0803315.1

(51) Int. Cl.
| | | |
|---|---|---|
| C07K 1/107 | (2006.01) | |
| C07K 1/113 | (2006.01) | |
| C07K 1/02 | (2006.01) | |
| C07K 1/13 | (2006.01) | |

(52) U.S. Cl.
CPC .............. *C07K 1/1133* (2013.01); *C07K 1/02* (2013.01); *C07K 1/026* (2013.01); *C07K 1/107* (2013.01); *C07K 1/13* (2013.01)

(58) Field of Classification Search
None
See application file for complete search history.

(56) References Cited

PUBLICATIONS

Chalker et al ('Methods for converting cysteine to dehydroalanine on peptides and proteins' Chemical Science 2011 v2 pp. 1666-1676).*
Sulc et al ('Efficient trapping of HNO by deoxymyoglobin' J. Am. Chem. Soc. 2004 v126 pp. 1096-1101).*
Tadross et al ('Remodelling by diversity and design' Nature Chemistry v4 Dec. 2012 pp. 963-965).*
Chalker et al ('Chemical modification of proteins at cysteine: opportunites in chemistry and biology' Chem. Asian J. v4 2009 pp. 630-640).*
UCSC Proteome browser (retrieved from https://genome.ucsc.edu/goldenPath/help/pbTracksHelpFiles/pbcCnt.shtml on Oct. 9, 2014, 2 pages).*
Smith et al ('The concept of a random coil residual structures in peptides and denatured proteins' Folding and Design v1(5) Oct. 1, 1996 pp. R95-R106).*
Price et al ('FastBLAST: Homology relationships for millions of proteins' PloS ONE v3(10) Oct. 2008 pp. 1-8).*
Digital biologist ('Protein engineering: lessons from the mother of invention' retrieved from http://www.digitalbiologist.com/2013/04/protein-engineering-learning-from-the-mother-of-invention.html on Sep. 17, 2014, 6 pages).*
Brocchieri et al ('Protein length in eukaryotic and prokaryotic proteomes' Nucleic acids research v33(10) 2005 pp. 3390-3400).*
Yamada, M et al., "Solid-Phase Synthesis of Dehydroalanine Derivatives." *Tetrahedron Letters*, Elsevier, 39 (3-4):289-292 (1998).
Wang, Jiangyun et al., "A biosynthetic route to dehydroalanine-containing proteins." *Angewandte Chemie* 46 (36): 6849-6851 (2007).
Okeley, N M et al., "Facile chemoselective synthesis of dehydroalanine-containing peptides." *Organic Letters*, 2 (23): 3603-3606 (2000).
Daniel, H Rich et al., "General Synthesis of didehydroamino acids and peptides." *Journal of the Chemical Society*, 897-898 (1974).
Matsuo Jun-Ichi et al., "Mild Preparation of alkenes from phenyl sulfides: one-pot elimination of phenylthio group via sulfilimine at ambient temperature." *Organic Letters*, 8(26): 6095-6098 (2006).
Bernardes, Goncalo et al., "Facile conversion of cysteine and alkyl cysteines to dehydroalanine on protein surfaces: versatile and switchable access to functionalized proteins." *Journal of the American Chemical Society* 130.15: 5052-5053 (2008).
Benjamin, G Davis, "Sugars and proteins: New strategies in synthetic biology." *Pure & Applied Chemistry* 81(2): 285-298 (2009).
"Artificial protein chemistry may be licensed to industry." *Chemistry World*, Oct. 8, 2008. Apr. 6, 2009 <http://www.rsc.org/chemistryworld/News/2008/October/08100801.asp>.
Lin Yuya A et al., "Allyl sulfides are priveledged substrates in aqueous cross-metathesis:application to site-selective protein modification." *Journal of the American Chemical Society*, 130 (30): 9642-9643 (2008).
Kirshenbaum, Kent et al., "Cross-dressing proteins by olefin metathesis." *Nature Chemical Biology*, 4(9): 527-528 (2008).
Cockroft, Scott L. and Lindsay, David M., "Highlights from 43$^{rd}$Euchem Conference on Stereochemistry." *Chem. Commun.*, 6441-6445 (2008).

* cited by examiner

*Primary Examiner* — Karlheinz R Skowronek
*Assistant Examiner* — Ronald Niebauer
(74) *Attorney, Agent, or Firm* — Rudy J. Ng; Carol L. Francis; Bozicevic, Field & Francis LLP

(57) ABSTRACT

The invention relates to methods for selectively converting a cysteine residue in a peptide or protein to the dehydroalanine (Dha) residue. The method also works on selenocysteine and substituted cysteine and selenocysteine residues, resulting in the Dha residue which may be converted to any natural or unnatural amino acid residue desired without the alteration of the remainder of the peptide or protein. The invention also allows ligation of a desired peptide at any point rather than at a point where there should be a naturally occurring cysteine, thereby allowing native chemical ligation to be used in the synthesis of peptides that do not contain cysteine. The methodology allows for the synthesis of very large peptides.

15 Claims, 9 Drawing Sheets

CHEMICAL MODIFICATION OF PROTEINS

RELATED APPLICATIONS

This application is the U.S. National Phase of International Application No. PCT/GB2009/000194, filed 23 Jan. 2009, published in English, which application claims priority under 35 U.S.C. §119 or 365 to Great Britain Application No. 0803315.1, filed 22 Feb. 2008. The entire teachings of the above applications are incorporated herein by reference.

TECHNICAL FIELD

The present invention relates to methods for chemically modifying proteins. Particularly, although not exclusively, the present invention relates to the transformation of cysteine residues to dehydroalanine in proteins and peptides, and to peptides and proteins modified in this way.

BACKGROUND

Genetic engineering has allowed both small and large peptides and proteins to be expressed in a number of different systems. Whilst some proteins manufactured in this way are suitable for therapeutic use, small differences in the way that the proteins are modified by the cells after they are made mean that often the intended therapeutic proteins are not exactly the same as those native proteins found in the animal or human to be treated.

Different systems produce different glycosylation patterns. For example some yeast expression systems do not glycosylate at all, and frog oocytes usually glycosylate in a different way to Chinese hamster ovaries. As a result, when these systems are used it is often desirable to subsequently modify the glycosylation pattern of the peptide or protein.

Much attention has focussed on enzymatic modification of proteins rather than chemical modification as enzymes tend to be able to carry out specific reactions in relatively mild conditions in which the protein to be modified will generally be stable. Chemical modification usually requires relatively harsher conditions and may, in some instances, be non-specific, and therefore give a number of different products that may need to be separated by, for example, chromatography.

Although chemical methods tend to be harsher and less specific than enzymatic methods, chemical modification can be carried out relatively quickly, with a minimum of laboratory equipment and with minimal expense. Methods are available for chemically modifying proteins, for example to attach sugars, and these methods generally involve chemical reaction of a side chain functional group such as asparagines, serine or threonine. Other amino acid side chain functionalities may also be reacted but further methods are desired and there is a need in the art for chemical methods of protein modification that are specific and which do not irreversibly affect amino acid side chains other than the target of modification.

It would also be useful if these chemical methods utilised a reaction that proceeded rapidly while preserving all other amino acid side chains.

The Merrifield solid state peptide synthesis has allowed the chemical synthesis of polypeptides to be carried out more efficiently than traditional solution chemistry. However, although the reactions are very nearly quantitative, small incremental losses of product and deviations from the desired amino acid order result in a practical limitation that render the method unfeasible for synthesis of polypeptides greater than about 70 residues in length. Thus, a large protein is generally chemically synthesised by coupling two or more synthesisable segments of the sequence together by native chemical ligation, a technique to react a peptide containing a C-terminal thioester with another peptide containing an N-terminal cysteine, in the presence of an exogenous thiol catalyst. Whilst this reaction proceeds with near quantitative yields, it is limited by the requirement that the resulting peptide had a cysteine residue at an appropriate position in the sequence.

It is an object of the invention to provide a method for chemically modifying proteins and peptides which addresses any limitations, needs or problems highlighted herein with the prior art methods or at least to provide the public and research community with a useful choice.

Documents cited in this specification are hereby incorporated by reference although no admission is made that any constitute prior art. The discussion of the documents states what their authors have asserted, and the applicants reserve the right to challenge the accuracy of the cited documents. Although prior art publications are referred to herein, this reference does not constitute an admission that any of these documents form part of the common general knowledge in the art in any country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning; that it will be taken to mean an inclusion of not only the listed components or steps it directly references, but also other non-specified components or elements. This rationale applies when the related terms 'comprised' or 'comprising' are used in relation to one or more steps in a method or process.

DISCLOSURE OF THE INVENTION

Figure 1:
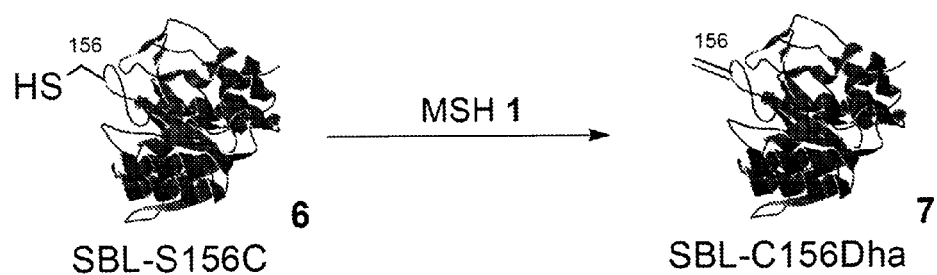
FIG. 1 shows a reaction scheme for the conversion of Cys156 to Dha156 on SBL (see Example 4), according to embodiments of the present disclosure.

According to a first aspect, the present invention provides a method for selectively converting an optionally substituted cysteine or selenocysteine residue in a peptide or protein to a dehydroalanine residue comprising the step of contacting the peptide or protein with a sulfonylhydroxylamine.

The cysteine or selenocysteine residue to be converted in the method of the invention may be substituted with an organic radical or may be unsubstituted. If substituted, the cysteine or selenocysteine is preferably alkyl substituted, more preferably methyl or ethyl substituted.

Throughout the specification reference will be made to a 'cysteine residue' and optionally substituted cysteine or optionally substituted selenocysteine are to be taken as included unless the context requires otherwise.

The sulfonylhydroxylamine for use in the method of the invention is preferably O-mesitylenesulfonylhydroxylamine (MSH). Although other sulfonylhydroxylamines may be used in the inventive method, O-mesitylenesulfonylhydroxylamine is particularly easy to use as it readily crystalises and is therefore easy to purify and to weigh.

Other agents suitable for effecting the inventive conversion conform to the general formula I,

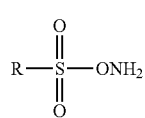

Formula I where R is an organic radical, preferably electron withdrawing and more preferably a substituted arene such as p-tolyl or also preferably trifluoromethyl.

Preferably the step of contacting the cysteine residue with the sulfonylhydroxylamine takes place in a solution or suspension in a solvent, preferably a polar aprotic solvent. The solvent may be water, methanol, ethanol, isopropanol or another alcohol or other polar protic solvent.

Preferred polar aprotic solvents for use in the method of the invention include 1,4-dioxane, tetrahydrofuran, dichloromethane, acetone, acetonitrile, dimethylformamide and dimethylsulfoxide. The most preferred solvent for use in the method of the invention is dimethylformamide (DMF).

In preferred embodiments the cysteine residue is at the surface of the peptide or protein. The reaction may however be carried out on a cysteine residue that is internal to the peptide in its natural state by denaturing the peptide reversibly, carrying out the method of the invention and then allowing the peptide to revert to its natural state.

The method of the invention may preferably be carried out in the presence of a base. The base may be the conjugate base of any standard buffer used in the fields of chemistry and biology, including for example Tris buffer, HEPES buffer or the base may be a phosphate buffer. When buffers are used as the base in the inventive method they preferably maintain pH in the range of about 6 to about 12, more preferably about 7 to about 10 and most preferably around pH 8. Particularly advantageous results may be obtained using a pH of between 7.5 and 8.5 and the most advantageous results have been obtained at pH 8. These pH values are preferred when using the inventive method.

In preferred embodiments the base is present as an aqueous solution of sufficient volume such that at least one equivalent of the base is dissolved. In preferred embodiments the base is an alkaline or alkaline earth carbonate, more preferably potassium carbonate made up in distilled water.

Preferably, in carrying out the method of the invention the peptide or protein is first dissolved in a solvent and mixed with base, and the resulting mixture is added dropwise to a solution of the sulfonylhydroxylamine. More preferably, the peptide/base solution is cooled, more preferably to around 0° C., and the sulfonylhydroxylamine is maintained at room temperature. More preferably, the peptide/base solution is added to the sulfonylhydroxylamine over between 1 and 10 minutes, preferably over between 2 and 5 minutes and most preferably over around 3 minutes.

The method of the invention may additionally comprise a subsequent step of reacting the carbon-carbon double bond of the dehydroalanine. To this end a number of examples are given in the following pages demonstrating reaction of the double bond to form a derivitised peptide or protein. Other examples show the conversion of the dehydroalanine to a natural amino acid side chain, thereby giving the overall effect of replacing cysteine with another amino acid.

In a preferred embodiment, the step of reacting the carbon-carbon double bond comprises an addition reaction. In particularly preferred embodiments the addition across the double bond of the dehydroalanine residue is stereoselective. Suitable methods of effecting stereoselective addition across a carbon-carbon double bond are well known to the person skilled in the art, and include but are not limited to use of chiral auxiliaries. The present application details methods suitable for use on peptides or proteins that have minimal impact on structure or other amino acids present therein.

In one embodiment of the invention the carbon-carbon double bond of the dehydroalanine is reacted with a thiol to form a thioether derivitised peptide or protein. In this way various moieties may be affixed to the peptide or protein such as sugars, amino acids and any desired group.

In a further aspect the present invention provides a method for ligating a first peptide or protein having a C-terminal thioester with a second peptide or protein having an N-terminal cysteine residue comprising effecting native chemical ligation, that is transthioesterification followed by a S→N acyl shift, to form a peptide bond between the first and second peptides or proteins and characterised in that the method comprises the additional step of converting the cysteine residue previously at the N terminus of the second peptide to a dehydroalanine residue by carrying out the step of contacting the peptide or protein with a sulfonylhydroxylamine.

The dehydroalanine residue formed in the ligated peptide or protein discussed immediately above may, in preferred embodiments, be subsequently reacted to form another amino acid, or to add a sugar or other peptide.

In line with the earlier discussion whereby cysteine and selenocysteine and their corresponding optionally substituted derivatives are incorporated within the term 'cysteine' for the purposes of this specification, the term thioester may comprise a selenoester and the 'native chemical ligation' reaction may be with either cysteine or selenocysteine such that the terms 'transthioesterification' and 'S→N acyl shift' may be technically an inaccurate description of the actual reaction. The definitions of the terms 'transthioesterification' and ' S→N acyl shift' are hereby extended to cover these additional embodiments of the inventive method.

In further aspects the present invention also provides a peptide or protein when made or modified according to methods of the invention. Many of these proteins will have application in the field of human therapeutics and so the invention also encompasses those modified peptides when incorporated into therapeutic dosage forms and the like.

The following detailed description appears as a commentary of the various examples using the inventive method followed by a discussion of the benefits and uses that the method of the invention has. The discussion is in no way to be considered as limiting the full scope of the invention as defined by the appended claims.

DETAILED DESCRIPTION OF THE INVENTION

Melting points were recorded on a Kofler hot block and are uncorrected. Proton nuclear magnetic resonance (δH) spectra were recorded on a Bruker AV400 (400 MHz), or on a Bruker AVII500 (500 MHz) spectrometer. Carbon nuclear magnetic resonance (δC) spectra were recorded on a Bruker AV400 (100.7 MHz) spectrometer or on a Bruker AVII500 (125.8 MHz) spectrometer. Spectra were fully assigned using COSY and HMQC; multiplicities were assigned using DEPT 135. All chemical shifts are quoted on the δ scale in ppm using residual solvent as the internal standard (1H NMR: $CDCl_3$=7.26, $CD_3OD$=4.87; $^{13}C$ NMR: $CDCl_3$=77.0; $CD_3OD$=49.0). The following splitting abbreviations were used: s=singlet, d=doublet, t=triplet, q=quartet, a=apparent.

Infrared spectra were recorded on a Bruker Tensor 27 Fourier Transform spectrophotometer using thin films on NaCl plates for oils and KBr discs for solids and crystals. Absorption maxima ($v_{max}$) are reported in wavenumbers (cm$^{-1}$) and classified as strong (s) or broad (br).

Low resolution mass spectra were recorded on a Micromass Platform 1 spectrometer using electrospray ionization (ESI) or using a Walters 2790-Micromass LCT electrospray ionization mass spectrometer. High resolution mass spectra were recorded on a Walters 2790-Micromass LCT electrospray ionization mass spectrometer. m/z values are reported in Daltons.

Optical rotations were measured on a Perkin-Elmer 241 polarimeter with a path length of 1 dm and are reported with implied units of $10^{-1}$ deg cm2 g$^{-1}$. Concentrations (c) are given in g/100 ml.

Thin layer chromatography (TLC) was carried out using Merck aluminium backed sheets coated with 60F$_{254}$ silica gel. Visualization of the silica plates was achieved using a UV lamp (λmax=254 nm), and/or ammonium molybdate (5% in 2M $H_2SO_4$), or potassium permanganate (5% in 1M NaOH). Flash column chromatography was carried out using BDH PROLAB® 40-63 mm silica gel (VWR).

Anhydrous solvents were purchased from Fluka or Acros except dichloromethane which was distilled over calcium hydride. All other solvents were used as supplied (Analytical or HPLC grade), without prior purification. Distilled water was used for chemical reactions and Milli-Q water for protein modifications. Reagents were purchased from Aldrich and used as supplied. 'Petrol' refers to the fraction of light petroleum ether boiling in the range 40-60° C. All reactions using anhydrous conditions were performed using flame-dried apparatus under an atmosphere of argon or nitrogen.

Protein Mass Spectrometry:

Liquid chromatography-mass spectrometry (LC-MS) was performed on a Micromass LCT (ESI-TOF-MS) coupled to a Waters Alliance 2790 HPLC using a Phenomenex Jupiter C4 column (250×4.6 mm×5 μm). Water:acetonitrile, 95:5 (solvent A) and acetonitrile (solvent B), each containing 0.1% formic acid, were used as the mobile phase at a flow rate of 1.0 mL min$^{-1}$. The gradient was programmed as follows: 95% A (5 min isocratic) to 100% B after 15 min then isocratic for 5 min. The electrospray source of LCT was operated with a capillary voltage of 3.2 kV and a cone voltage of 25 V. Nitrogen was used as the nebulizer and desolvation gas at a total flow of 600 l hr$^{-1}$. Spectra were calibrated using a calibration curve constructed from a minimum of 17 matched peaks from the multiply charged ion series of equine myoglobin, which was also obtained at a cone voltage of 25 V. Total mass spectra were reconstructed from the ion series using the MaxEnt algorithm preinstalled on MassLynx software (v. 4.0 from Waters) according to manufacturer's instructions.

Example 1 methyl 2-[(tert-butoxycarbonyl)amino]acrylate

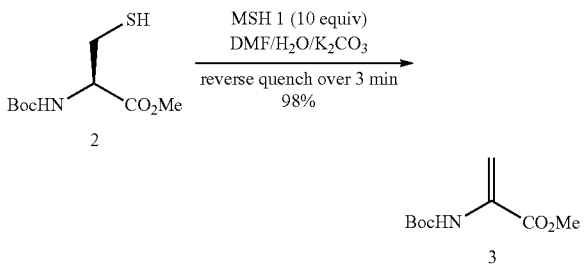

MSH 1 (439 mg, 2.0 mmol) was added to a 10 mL round bottom flask and dissolved in DMF (3 mL). In a separate vial, N-(tert-butoxycarbonyl)-L-cysteine methyl ester 2 (48 mg, 0.20 mmol) was added and dissolved in DMF (3 mL). The vial was cooled to 0° C. and a solution of potassium carbonate (138 mg, 1.0 mmol) in water (3.0 mL) was added. The resulting solution was added dropwise by pipette over a period of 3 min to the stirred MSH solution at room temperature. The vial was rinsed with DMF (2×1 mL) to ensure complete transfer. TLC (petrol:ethyl acetate, 4:1) analysis after completion of the addition revealed a single, UV active product (R$_f$ 0.6). The reaction mixture was transferred to a separatory funnel and diluted with diethyl ether (150 mL) and water (100 mL). After separation, the organic layer was washed successively with water (80 mL) and brine (80 mL) before drying (MgSO$_4$) and filtering. The solvent was removed under reduced pressure and the resulting residue purified by column chromatography to provide methyl 2-[(tert-butoxycarbonyl)amino]acrylate 3 as a clear oil (40 mg, 98%).

Data for Methyl 2-[(tert-butoxycarbonyl)amino]acrylate (BocCysOMe) 3: νmax (thin film) 3423, 2980, 1719, 1634, 1513, 1328, 1159, 1068 cm-1; δH (400 MHz, CDCl3) 1.46 (9H, s, C(CH3)3), 3.80 (3H, s, OCH3), 5.70 (1H, d, J 1.5 Hz, C=CHH), 6.13 (1H, app s, C=CHH), 7.00 (1H, br s, NH); δC (100.7 MHz, CDCl3) 28.2 (q, C(CH3)3), 52.8 (q, OCH3), 80.6 (s, C(CH3)3), 105.1 (t, C=CH2), 131.3 (s, C=CH2), 152.5, 164.4 (2×s, 2×CO). Found: C, 53.95%; H, 7.63%, N, 6.83%. C9H15NO4 requires: C, 53.72%; H, 7.51%; N, 6.96%.

Example 2

Methionine Recovery from Corresponding Sulfilimine

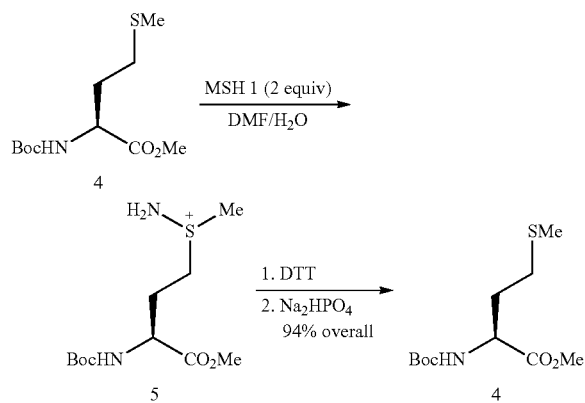

N-(tert-Butoxycarbonyl)-L-methionine methyl ester 4 (245 mg, 0.93 mmol) was added to a 50 mL round bottom flask and then dissolved in DMF (5 mL). The solution was stirred vigorously while water (5 mL) was added by pipette. MSH 1 (400 mg, 1.86 mmol) was added to the solution in one portion and the cloudy suspension homogenized after 30 seconds of stirring. After 5 minutes, TLC analysis revealed complete consumption of 4. All material was located on the baseline, and no sulfoxide 18 or sulfone 19 was detected. After 20 minutes of stirring, DTT (1.43 g, 1.86 mmol) was added as a solid. TLC analysis revealed no change after 1 hour of stirring. After 1 hour of total reaction time, Na2HPO4.12H2O (3.33 g, 9.30 mmol) was added to give a saturated solution of phosphate salts. After 2 hours of total reaction time (1 hour with base), TLC (30% ethyl acetate in petrol) revealed the regeneration of 4. A final hour of reaction time revealed no further change. The reaction was then diluted with diethyl ether (150 mL) and water (150 mL) and separated. The organic layer was washed sequentially with water (150 mL) and brine (150 mL), dried (MgSO4), filtered, and concentrated under reduced pressure. The product was purified by column chromatography (30% ethyl acetate in petrol) to give recovered N-(tert-butoxycarbonyl)-L-methionine methyl ester 4 (230 mg, 94%).

Data for N-(tert-Butoxycarbonyl)-L-methionine methyl ester 4: $[\alpha]_D^{20}$ −29.5 (c, 1 in MeOH) [Lit. $[\alpha]_D^{25}$ −34.0 (c, 1.0 in MeOH)][5]; δH (400 MHz, CDCl3) 1.39 (9H, s, C(CH3)3), 1.88 (1H, m, CHHCH2SCH3), 2.04-2.12 (4H, m, SCH3, CHHCH2SCH3), 2.49 (2H, t, J 8.0, CH2SCH3), 3.70 (3H, s, CO2CH3), 4.37 (1H, q, J 7.1, αH), 5.20 (1H, d, J 7.1, NH); δC (100.7 MHz, CDCl3) 15.3 (q, SCH3), 28.1 (q, C(CH3)3), 29.8 (t, CH2CH2SCH3), 31.9 (t, CH2SCH3), 52.2 (q, CO2CH3), 52.6 (d, αC), 79.8 (s, C(CH3)3), 155.2 (s, CO), 172.7 (s, CO2CH3).

Example 3

Regeneration of BocDhaOMe 3 from BocCys(SEt)OMe 15

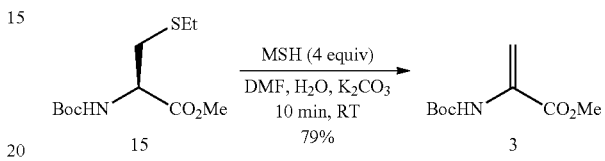

N-(tert-Butoxycarbonyl)-ethylthio-L-cysteine methyl ester 15 (106 mg, 0.40 mmol) was added to a 50 mL round bottom flask and dissolved in DMF (5 mL). Potassium carbonate (278 mg, 2.01 mmol) was added by pipette as a solution in water (1.0 mL). MSH 1 (172 mg 0.80 mmol) was added as a solid in one portion (open air, room temperature). TLC analysis (ethyl acetate:petrol; 1:4) after 1 min of reaction revealed a strongly UV active product ($R_f$ 0.6) and a trace of starting material ($R_f$ 0.5). A second dose of MSH 1 (172 mg 0.80 mmol) was added after 5 min of reaction time and TLC analysis revealed only the UV active product. After 10 min of total reaction time, the reaction mixture was diluted with diethyl ether (100 mL) and water (50 mL). The organic layer was separated and the aqueous layer was extracted with diethyl ether (2×50 mL). The combined organics were dried (MgSO4), filtered, and the solvent removed by rotary evaporation. Column chromatography (3% ethyl acetate in petrol) provided methyl 2-[(tert-butoxycarbonyl)amino]acrylate 3 (63 mg, 79%); this material was spectroscopically identical to that obtained from N-(tert-butoxycarbonyl)-L-cysteine methyl ester 2.

Example 4

Conversion of Cys156 to Dha156 on SBL

FIG. 1 shows a reaction scheme for the conversion of Cys156 to Dha156 on SBL.

All manipulations were carried out in a cold room at 4° C. Lyophilized SBL-S156C 6 (2.5 mg, 0.094 (mol) was dissolved in 2.50 mL of pH 8.0 sodium phosphate buffer (50 mM) in a 1.5 mL plastic tube. A solution of MSH was prepared in a separate tube by dissolving 4.0 mg (18.6 μmol) in 250 μL DMF. 125 μL of the MSH solution (9.3 μmol) was added by micropipette to the protein solution and the reaction was vortexed periodically over 1 minute. The tube was left to shake for an additional 19 minutes after which time a 30 μL aliquot was analyzed by LC-MS. A single protein species was detected with a mass of 26681, corresponding to the mass of SBL-C156Dha 7 (26681=calculated mass). Small molecules were removed from the reaction mixture by loading the sample onto a PD10 desalting column (GE Healthcare) previously equilibrated with 10 column volumes of pH 8.0 sodium phosphate buffer (50 mM) and eluting with 3.50 mL of the same buffer. The collected sample (now diluted to 0.7 mg/mL) was split into 200 μL aliquots, flash frozen with liquid nitrogen, and stored at −80° C.

The same reaction conditions were used and modified where appropriate according to the following table, Table 1, where the percentage conversions show the broad range of buffers are all suitable for carrying out the method of the invention.

TABLE 1

Conversion of Cys to Dha on SBL-S156C.

| Entry | MSH (equiv) | Buffer | pH | time (min) | Conv. % |
|---|---|---|---|---|---|
| 1 | 100 | TRIS (50 mM) | 8.0 | 20 | 50 |
| 2 | 100 | TAPS (50 mM) | 8.0 | 20 | 60 |
| 3 | 100 | Carbonate (50 mM) | 8.0 | 20 | 50 |
| 4 | 60 | Carbonate (100 mM) | 9.6 | 10 | 40 |
| 5 | 100 | Carbonate (100 mM) | 9.6 | 120 | 50 |
| 6 | 20 | Phosphate (50 mM) | 8.0 | 20 | 10 |
| 7 | 50 | Phosphate (50 mM) | 8.0 | 20 | 20 |
| 8 | 100 | Phosphate (50 mM) | 8.0 | 1 | 25 |
| 9 | 100 | Phosphate (50 mM) | 8.0 | 10 | 60 |
| 10 | 100 | Phosphate (50 mM) | 8.0 | 20 | >95 |
| 11 | 100 | Phosphate (50 mM) | 7.5 | 20 | 90 |
| 12 | 100 | Phosphate (50 mM) | 6.5 | 20 | 40 |

Example 5

One-Pot Conversion of SBL-S156C to SBL-C156SGlcNAc

Figure 2:
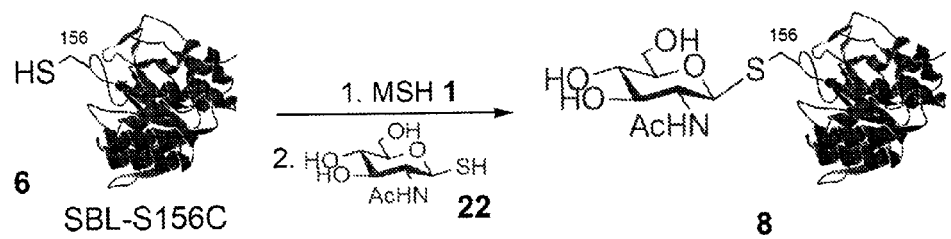
FIG. 2 shows a reaction scheme for the one-pot conversion of SBL-S156C to SBL-C156SGlcNAc (see Example 5), according to embodiments of the present disclosure.

FIG. 2 shows a reaction scheme for the one-pot conversion of SBL-S156C to SBL-C156SGlcNAc.

All manipulations were carried out in a cold room maintained at 4° C. A 1 mg sample of lyophilized SBL-S156C 6 (0.037 μmol) was dissolved in 1.0 mL in pH 8.0 sodium phosphate buffer (50 mM). A solution of MSH 1 was prepared by dissolving 1.8 mg (8.36 μmol) in 100 μL DMF. A 50 μL portion of the MSH solution was added to the protein by micropipette. The reaction was vortexed periodically over 1 minute and then rotated on a lab rotisserie for an additional 19 minutes at 4° C. A 50 μL aliquot was analyzed by LC MS to confirm the conversion of Cys156 to Dha156 (26681 calculated, 26681 found). To the reaction mixture was added 1-thio-2-acetamido-2-deoxy-β-D-glucopyranose 22 as a solid (8.8 mg, 1000 eq) to give a 39 mM solution in thiol. After 90 minutes of shaking at 4° C., the reaction was analyzed directly by LC-MS. Complete conversion to SBL-C156SGlcNAc 8 was observed (calculated mass, 26918; observed mass, 26918).

Example 6

One-Pot Conversion of SBL-S156C to SBL-C156SMan

Figure 3:
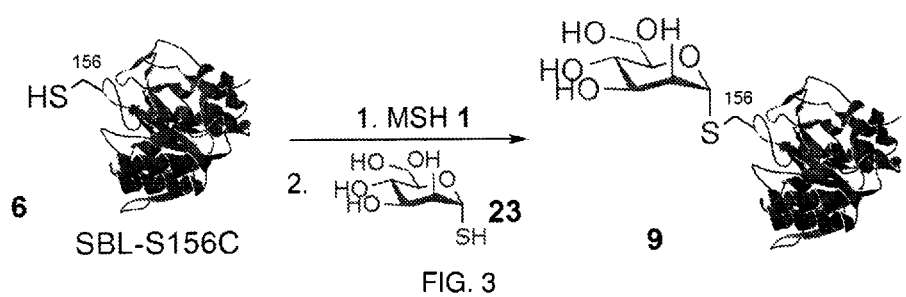
FIG. 3 shows a reaction scheme for the one-pot conversion of SBL-S156C to SBL-C156SMan (see Example 6), according to embodiments of the present disclosure.

FIG. 3 shows a reaction scheme for the one-pot conversion of SBL-S156C to SBL-C156SMan. An analogous procedure to that above was followed for the conversion of SBL-S156C 6 to SBL-C156SMan 9. LC-MS analysis revealed full conversion to the desired glycoprotein 9 (calculated mass, 26877; observed mass, 26877).

Example 7

Conjugation of Glutathione to SBL-C156Dha 7

Figure 4:
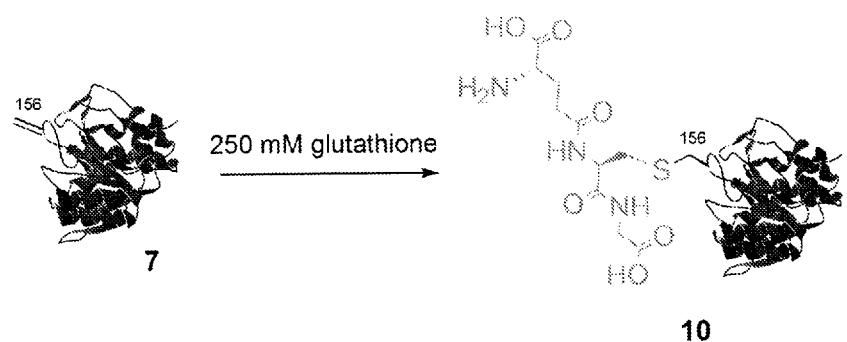
FIG. 4 shows a reaction scheme for the conjugation of glutathione to SBL-C156Dha 7 (see Example 7), according to embodiments of the present disclosure.

FIG. 4 shows a reaction scheme for the conjugation of glutathione to SBL-C156Dha 7.

All manipulations were carried out in a cold room maintained at 4° C. A 200 μL aliquot of 0.7 mg/mL SBL-C156Dha 7 previously prepared was thawed and kept on ice until needed. Glutathione (GSH) (16.1 mg, 0.05 mmol) and potassium phosphate dibasic (46 mg) were both added as solids to a 1.5 mL plastic tube and dissolved in 150 (L water (MilliQ). The solution of GSH was then added to the protein solution (pH of reaction 9.0) and vortexed over 1 min. The reaction was shaken for an additional 90 minutes. LC-MS analysis of the reaction mixture revealed near complete conversion to SBL-C156SGSH 10 (calculated mass, 26988, observed mass, 26987).

Example 8

Monomethyl Lysine Analog 11

Figure 5:
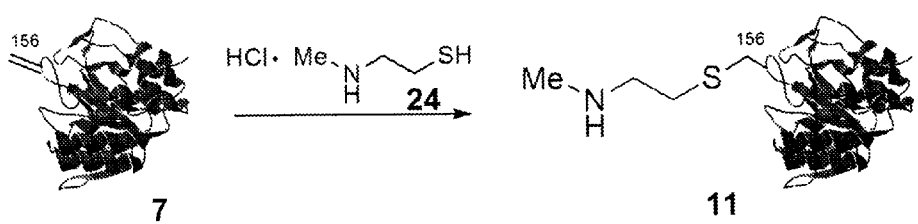
FIG. 5 shows a reaction scheme for the preparation of monomethyl lysine analog 11 (see Example 8), according to embodiments of the present disclosure.

FIG. 5 shows a reaction scheme for the preparation of monomethyl lysine analog 11.

All manipulations were carried out in a cold room maintained at 4° C. A 200 μL aliquot of 0.7 mg/mL SBL-C156Dha 7 previously prepared was thawed and kept on ice until needed. A solution of 2-(methylamino)ethanethiol hydrochloride 24 was prepared by dissolving 6.6 mg (0.052 mmol) in 200 μL water (MilliQ). Potassium phosphate dibasic (45 mg, 0.26 mmol) was added to the thiol solution as a solid and the solution vortexed. All of the thiol solution was transferred to the protein by micropipette to give a reaction mixture of pH 9.0. The reaction was vortexed and then shaken at 4° C. for 90 minutes. LC-MS analysis revealed full conversion to the monomethyl lysine analog 11 (calculated mass, 26772; observed mass 26773).

Example 9

Dimethyl Lysine Analog

Figure 6:
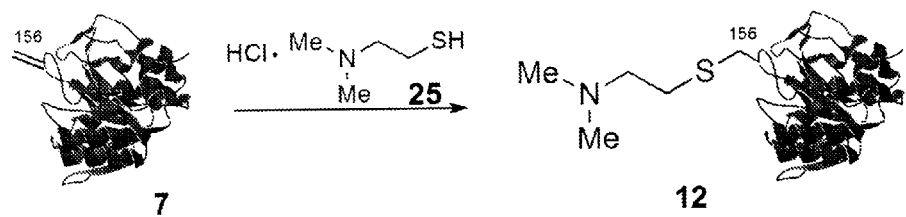
FIG. 6 shows a reaction scheme for the preparation of dimethyl lysine analog 12 (see Example 9), according to embodiments of the present disclosure.

FIG. 6 shows a reaction scheme for the preparation of dimethyl lysine analog 12.

All manipulations were carried out in a cold room maintained at 4° C. A 200 μL aliquot of 0.7 mg/mL SBL-C156Dha 7 previously prepared was thawed and kept on ice until needed. A solution of 2-(dimtheylamino)ethanethiol hydrochloride 25 was prepared by dissolving 3.2 mg (0.022 mmol) in 150 μL of pH 8.0 phosphate buffer (50 mM). A 50 μL aliquot of the thiol solution was added to the protein and the reaction was shaken at 4° C. for 90 minutes at which time a 40 μL aliquot was taken for LC-MS analysis. Full conversion to the desired dimethyl lysine analog 12 was observed (calculated mass, 26786; observed mass, 26787).

Example 10

Trimethyl Lysine Analog

Figure 7:
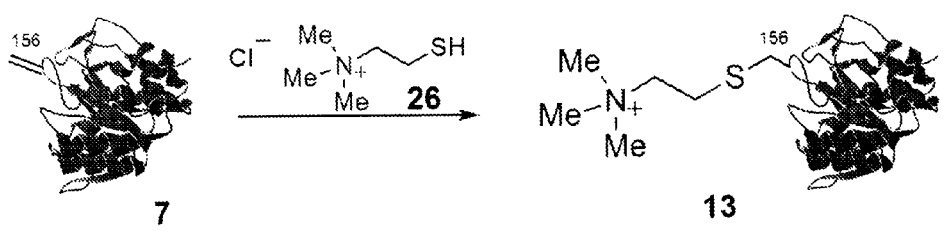
FIG. 7 shows a reaction scheme for the preparation of trimethyl lysine analog 13 (see Example 10), according to embodiments of the present disclosure.

FIG. 7 shows a reaction scheme for the preparation of trimethyl lysine analog 13.

All manipulations were carried out in a cold room maintained at 4° C. A 200 μL aliquot of 0.7 mg/mL SBL-C156Dha 6 previously prepared was thawed and kept on ice until needed. A solution of 2-(mercaptoethyl)trimethylammonium chloride 26 was prepared by dissolving 8.2 mg of 26 (0.052 mmol) and 27 mg potassium phosphate dibasic (0.20 mmol) in 200 μL of water (MilliQ). All of the thiol solution was added to protein to give a reaction mixture at pH 9.0. The reaction was shaken at 4° C. for 90 min before a 50 μL aliquot was analyzed by LC-MS. Full conversion to the trimethyl lysine analog 13 was observed (calculated mass, 26801; observed mass, 26801).

Example 11

SBL-C156Farnesyl

Figure 8:
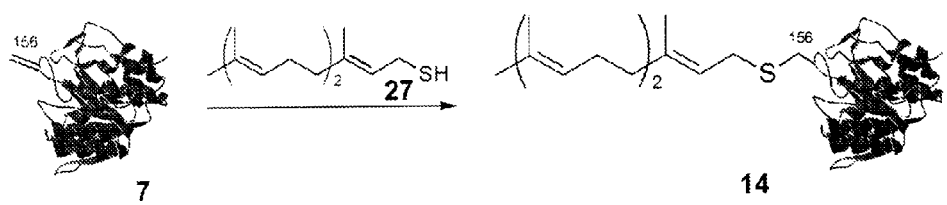
FIG. 8 shows a reaction scheme for the preparation of SBL-C156Farnesyl 14 (see Example 11), according to embodiments of the present disclosure.

FIG. 8 shows a reaction scheme for the preparation of SBL-C156Farnesyl 14.

A 200 μL aliquot of 0.7 mg/mL SBL-C156Dha 7 previously prepared was thawed. A (0.35 M) farnesyl thiol 27 solution in DMSO was prepared alongside an aqueous solution of TCEP.HCl (tris(2-carboxyethyl) phosphine chloride). The TCEP was neutralized to pH 7.0 with sodium hydroxide to give a final concentration of 0.20 M TCEP. The farnesyl thiol 27 (15 μL) and TCEP solution (52 μL) were added in succession to the protein to give a cloudy emulsion. The reaction was rotated on a lab rotisserie for 90 minutes at room temperature and then analyzed directly by LC-MS. A protein species with a mass of 26940 was found which corresponds to the farnesyl thioether sodium adduct (calculated mass, 26941).

Example 12

Activity Assay for SBL-SGlcNAc 8

The enzyme concentration was determined using the bicinchoninic acid protein assay (Pierce) with bovine serum albumin as a standard. Turnover numbers are based on an enzyme monomer.

TABLE 2

| | kinetics data | | |
|---|---|---|---|
| SBL | $K_m$ (mM) | $k_{cat}$ (s$^{-1}$) | $k_{cat}/K_m$ (M$^{-1}$ s$^{-1}$) |
| SBL-S156C 6 | 0.83 ± 0.07 | 27.1 ± 0.7 | (3.3 ± 0.1) × 10$^4$ |
| SBL-SGlcNAc 8 | 0.72 ± 0.09 | 5.7 ± 0.2 | (7.9 ± 0.3) × 10$^3$ |

Initial velocities for SBL-S156C and SBL-SGlcNAc 8 were determined using suc-AAPF-pNA (Bachem Biosciences Inc) with continuous detection of the formation of the product pNA at 410 nm (pNA: $\epsilon$=8,800 M$^{-1}$ cm$^{-1}$) at 25° C. A typical reaction mixture contained 100 mM sodium phosphate, pH 7.5, 500 mM NaCl, 1 mM suc-AAPF-pNA in a final volume of 1 ml. Reactions were initiated by the addition of enzyme, typically 15 nM final concentration. Initial velocity kinetic data were fitted using GraFit 5.

Example 13

Chemical Incorporation SEt-Cys

Figure 9:
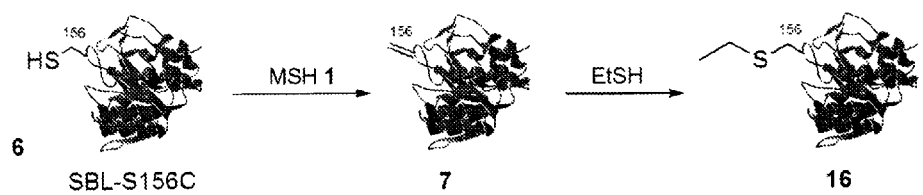
FIG. 9 shows a reaction scheme for chemical incorporation SEt-Cys (see Example 13), according to embodiments of the present disclosure.

FIG. 9 shows a reaction scheme for chemical incorporation SEt-Cys.

A fresh sample of SBL-156Dha 7 was prepared as described above by the action of MSH on cysteine and used directly. Accordingly, 35 μL of ethanthiol was added directly to a 625 μL of a 1 mg/mL solution of SBL-156Dha 6 (0.05 μmol) in 50 mM sodium phosphate (pH 8.0). The sample was vortexed to homogenize and then rotated for 30 minutes at room temperature. LC-MS analysis of the reaction mixture showed full conversion to the ethyl thioether protein 16 (calculated mass, 26743, observed mass, 26746). The reaction mixture was passed through a PD10 column to remove the bulk of small molecules, eluting with pH 8.0 sodium phosphate (50 mM) and then purified twice by dialysis against 4 L of the same buffer to remove remaining small molecules. After dialysis the sample concentration was ~0.36 mg/mL.

Example 14

Preparation of SBL-C156SGlcNAc

Figure 10:
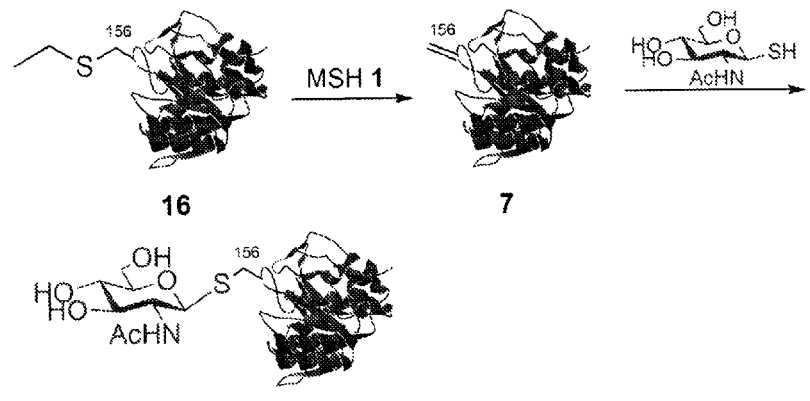
FIG. 10 shows a reaction scheme for the preparation of SBL-C156SGlcNAc (see Example 14), according to embodiments of the present disclosure.

FIG. 10 shows a reaction scheme for the preparation of SBL-C156SGlcNAc.

A 500 μL sample of SBL-156SEt 16 was thawed and kept on ice until needed. An MSH solution (1.8 mg, 8 μmol) was prepared in DMF (720 μL) and 14 μL (0.16 μmol) was added to a 250 μL sample of SBL-156SEt 16. The reaction was vortexed to homogenize and then shaken for 20 minutes at 4° C. A 40 μL aliquot was taken for LC-MS analysis that showed full conversion to SBL-C156Dha 7 (calculate mass, 26681; observed mass, 26685). To verify that this material corresponds to the dehydroalanine containing protein, GlcNAc-SH 22 (4 mg, 16.9 μmol) was added as a solid to the reaction mixture and rotated at room temperature for 30 min. Full conversion to SBL-C156SGlcNAc 8 confirmed the regeneration of dehydroalanine (calculated mass, 26918; observed mass, 26920).

In order to carry out experiments on native chemical ligation and subsequent modification of cysteine residues a model cysteine containing dipeptide was first made.

Example 15

Native Chemical Ligation: BocAlaCysOMe 18

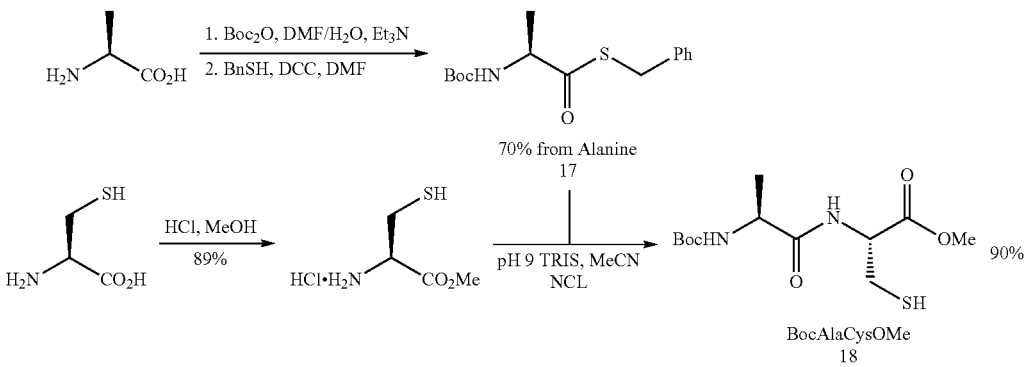

Native Chemical Ligation: BocAlaCysOMe

L-Cysteine methyl ester hydrochloride (5.0 g, 29.10 mmol) was added to a 100 mL, 2-neck round bottom flask and dissolved in 15 mL of pH 8.0 TRIS (50 mM). The solution was cooled to 0° C. and 5.0 mL of 5.82 M NaOH was added dropwise. BocAlaSBn 17 (2.50 g, 8.46 mmol) was added as a solution in MeCN (25 mL). The resulting solution (pH 9.0, pH paper), was stirred at room temperature for 5 hours after which time TLC indicated complete comsumption of thioester 17 ($R_f$=0.38, 10% EtOAc in petrol) and formation of the ligated product 18 ($R_f$=0.50, 50% EtOAc in petrol). Tributylphosphine (1.05 mL, 4.26 mmol) was added to reduce any disulfide and after 15 min the reaction was diluted with $Et_2O$ (250 mL) and $H_2O$ (150 mL). The layers were separated and the aqueous later was extracted with $Et_2O$ (100 mL). The combined organics were washed with $H_2O$ (2×150 mL) and brine (150 mL) and then dried ($MgSO_4$), filtered, and concentrated under reduced pressure. Purification by column chromatography (10% EtOAc in petrol to 50% EtOAc in petrol) provided the coupled product 18 as white crystals (2.592 g, 90%). m.p.=101-102° C.; $[\alpha]^{20}_D$=−1.9° (c=1.0, $CHCl_3$); IR (KBr): 3387, 3298, 2979, 2565, 1746, 1700, 1653, 1503, 1443, 1390, 1362, 1308; $^1$H NMR ($CDCl_3$, 400 MHz): δ=7.13 (1H, d, J=5.8, $NH_{Cys}$), 5.24 (1H, d, J=6.1, $NH_{Ala}$), 4.82 (1H, ddd, J=7.8, 4.3, 4.0, $H_{\alpha\ Cys}$), 4.21 (1H, br. m, $H_{\alpha\ Ala}$), 3.75 (3H, s, $CO_2CH_3$), 3.03-2.90 (2H, m, $CH_2SH$), 1.50 (1H, t, J=8.7, SH), 1.41 (9H, s, Boc), 1.35 (3H, d, J=7.1, $CH_{3\ Ala}$); $^{13}$C NMR (100 MHz): δ=172.7, 170.3, 155.5 (3×C=O), 80.1 (Boc), 53.7 ($C_{\alpha\ Cys}$), 52.8 ($CO_2CH_3$), 50.1 ($C_{\alpha\ Ala}$), 28.3 (Boc), 26.6 ($CH_2SH$), 17.9 ($CH_{3\ Ala}$); HRMS m/z (EI+). Found 329.1142 (M+Na)$^+$; $C_{12}H_{22}N_2O_5SNa$ requires 329.1147. Analysis for $C_{12}H_{22}N_2O_5S$: C, 47.04; H, 7.24; N, 9.14. Found: C, 47.05; H, 7.25; N, 9.09.

Example 16

Conversion of BocAlaCysOMe to BocAlaDhaOMe

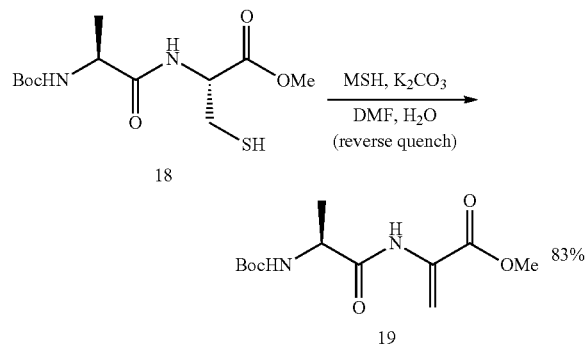

MSH (1) (702 mg, 3.26 mmol) was added to a 50 mL round bottom flask and dissolved in DMF (3 mL). In a separate glass vial, BocAlaCysOMe (18) (100 mg, 0.326 mmol) was dissolved in DMF (5 mL) and cooled on ice. A solution of $K_2CO_3$ (225 mg, 1.63 mmol) in $H_2O$ (5 mL) was added to the peptide solution. The resulting solution of 18 was then added dropwise by pipette to the stirred solution of MSH over a period of 5 min. After completion of the addition, TLC (50% EtOAc in petrol) revealed complete comsumption of peptide 18 ($R_f$=0.49) and the formation of BocAlaDhaOMe ($R_f$=0.74). The reaction was diluted with $Et_2O$ (250 mL) and $H_2O$ (200 mL). After separation, the organic layer was washed with $H_2O$ (150 mL) and brine (150 mL). After drying ($MgSO_4$), the organics were filtered and the solvent was removed under reduced pressure. The product was purified by column chromatography (20% EtOAc in petrol) to give 74 mg of the titled compound 19 as a clear, thick oil (83% yield). IR (film): 3332, 2980, 1691, 1523, 1442, 1368, 1327, 1249, 1167; $^1$H NMR ($CDCl_3$, 400 MHz): δ=8.46 (1H, br. s, $NH_{Dha}$), 6.60 (1H, app. s, C=CHH), 5.91 (1H, d, J=1.3, C=CHH), 5.01 (1H, app. br. s, $NH_{Ala}$), 4.26 (1H, app. br. s, $H_{\alpha\ Ala}$), 3.84 (3H, s, $CO_2CH_3$), 1.46 (9H, s, Boc), 1.40 (3H, d, J=7.3, $CH_{3\ Ala}$); HRMS m/z (EI+). Found 295.1264 (M+Na)$^+$; $C_{12}H_{20}N_2O_5Na$ requires 295.1270.

Example 17

Conversion of BocAlaDhaOMe to BocAlaLeuOMe

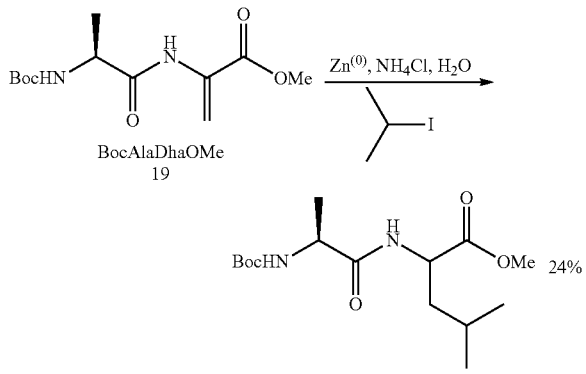

BocAlaDhaOMe 19 (43 mg, 0.16 mmol) was added to a 50 mL 2-neck round bottom flask and flushed with argon before dissolving in 1,4-dioxane (1.0 mL). Saturated $NH_4Cl$ (3 mL, aqueous solution) was added to the vigorously stirred solution followed by isopropyl iodide (80 μL, 0.79 mmol) and zinc dust (105 mg, 1.60 mmol). The reaction was stirred vigorously (>1000 rpm) at room temperature for 1.5 hours before a second portion of zinc (105 mg, 1.60 mmol) and isopropyl iodide was added (80 μL, 0.79 mmol). After 3 hours of total reaction time, TLC (45% EtOAc in Petrol) indicated complete consumption of starting material. The reaction was diluted with $Et_2O$ (150 mL) and washed successively with $H_2O$ (150 mL) and brine (2×150 mL). The organic layer was dried ($MgSO_4$), filtered, and the solvent removed under reduced pressure. Purification by column chromatography (35% EtOAc in Petrol) provided BocAlaLeuOMe 20 as a mixture of diastereomers (12 mg, 24%). (Yield unoptimized, 1$^{st}$ native chemical ligation at Ala-Leu). $^1$H NMR ($CDCl_3$, 400 MHz): δ=6.56 (1H, d, J=6.5, $NH_{Leu}$), 4.98 (1H, br. s, $NH_{Ala}$), 4.61 (1H, td, J=8.6, 4.6), 4.19 (1H, br. s, $H_{\alpha\ Ala}$), 3.73 (3H, s, $CO_2Me$), 1.67-1.43 (3H, m, $CH_2CHMe_2$) 1.46 (9H, s, Boc), 1.38-1.35 (3H, m, $CH_{3\ Ala}$) 0.95-0.92 (6H, m, 2× $CH_{3\ Leu}$). LRMS (m/z, ESI+): 317 (M+H), 339 (M+Na).

Example 18

Conversion of BocAlaDhaOMe to BocAlaPheOMe

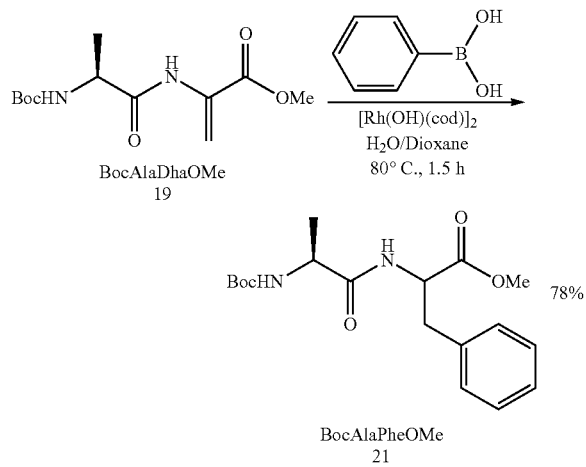

BocAlaDhaOMe 19 (50 mg, 0.18 mmol) was added to a 2-neck round bottom flask and placed under an argon atmosphere before dissolving in 1,4-dioxane (3.0 mL). H$_2$O (0.30 mL) was added to the stirred solution followed by phenylboronic acid (69 mg, 0.55 mmol) and rhodium(I)hydroxide cyclooctadiene dimer ([Rh(OH)(cod)]$_2$, 4.0 mg, 0.009 mmol). All were added under a stream of argon. The reaction mixture was lowered into an oil bath preheated to 80° C. and stirred for 1.5 hours after which time no starting material was detected by TLC (25% EtOAc in petrol). The reaction was diluted with Et$_2$O (100 mL) and washed successively with H$_2$O (2×100 mL) and brine (100 mL). The organic layer was dried over MgSO$_4$ and filtered. The solvent was removed under reduced pressure and the residue purified by column chromatography (45% EtOAc in petrol) to afford BocAlaPheOMe 21 as a mixture of diastereomers (50 mg, 78%). $^1$H NMR (CDCl$_3$, 400 MHz): δ=7.30-7.08 (5H, m, Ar), 6.75-6.61 (1H, m, NH$_{Phe}$), 5.03 (1H, br. s, NH$_{Ala}$), 4.85 ($^1$H, m, H$_{\alpha\,Phe}$) 4.16 (1H, br. s, H$_{\alpha\,Ala}$), 3.71 (3H, s, CO$_2$Me), 3.18-3.04 (2H, m, CH$_2$Ph), 1.43 (9H, s, Boc), 1.31-1.28 (3H, 2×d for each diastereomer, J=7.1, 7.3, CH$_{3\,Ala}$). d.r.=1.5:1.0, based on integration of two Me$_{Ala}$ doublets at 1.31 and 1.28. HRMS m/z (ESI+). Found 373.1734 (M+Na)$^+$; C$_{18}$H$_{26}$N$_2$O$_5$Na requires 373.1739.

Example 19

Conversion of BocAlaDhaOMe to BocAlaTyrOMe

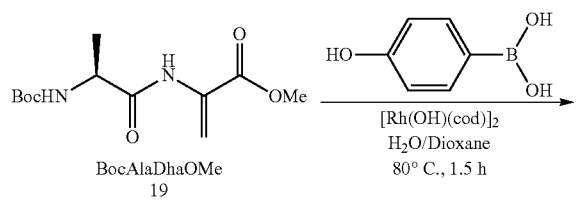

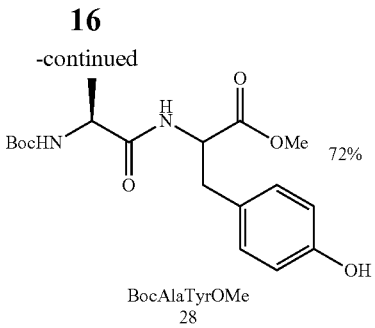

BocAlaDhaOMe 19 (50 mg, 0.18 mmol) was added to a 25 mL 2-neck round bottom flask and placed under an argon atmosphere before 1,4-dioxane (3.0 mL) and H$_2$O (0.30 mL) were added. 4-hydroxyphenylboronic acid (76 mg, 0.55 mmol) and rhodium(I)hydroxide cyclooctadiene dimer ([Rh(OH)(cod)]$_2$, 4.0 mg, 0.009 mmol) were both added under a stream of argon. The stirred reaction mixture was lowered into an oil bath preheated to 80° C. and stirred for 1.5 hours at which time TLC revealed complete consumption of starting material (50% EtOAc in petrol). The reaction was diluted with Et$_2$O (100 mL) and washed successively with H$_2$O (2×100 mL) and brine (100 mL). The organic layer was dried (MgSO$_4$) and filtered. The solvent was removed under reduced pressure and the residue purified by column chromatography (gradient from 20% to 50% EtOAc in petrol) to afford BocAlaTyrOMe 28 as a mixture of diastereomers (48 mg, 72%). $^1$H NMR (CDCl$_3$, 400 MHz): δ=7.04-6.66 (5H, m, Ar$_{Tyr}$ and NH$_{Tyr}$), 5.16 (1H, br. s, NH$_{Ala}$), 4.82 (1H, m, H$_{\alpha\,Tyr}$), 3.72 (3H, s, CO$_2$Me), 3.03 (m, 2H, CH$_2$Ar), 1.46 (9H, s, Boc), 1.26 (3H, m, CH$_{3\,Ala}$). LRMS (m/z, ESI+): 367 (M+H)$^+$, 389 (M+Na)$^-$.

Example 20

Conversion of SBL-C156Dha to the Histidine Isostere

Figure 11:
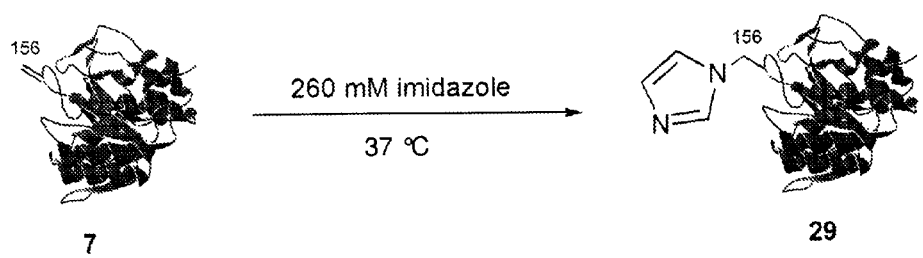
FIG. 11 shows a reaction scheme for conversion of SBL-C156Dha to the histidine isostere (see Example 20), according to embodiments of the present disclosure.

FIG. 11 shows a reaction scheme for conversion of SBL-C156Dha to the histidine isostere.

A 200 µL aliquot of 0.7 mg/mL SBL-C156Dha 7 previously prepared was thawed. Imidazole (3.6 mg, 0.052 mmol) was added to the protein solution as a solid. The reaction was incubated at 37° C. and analyzed by LCMS at 2, 4, and 5 hours after which time complete conversion to the histidine isostere 29 was observed. (Calculated mass=26749. found=26749).

Example 21

Conversion of SBL-C156Dha to SBL-Dha156Ala

Figure 12:
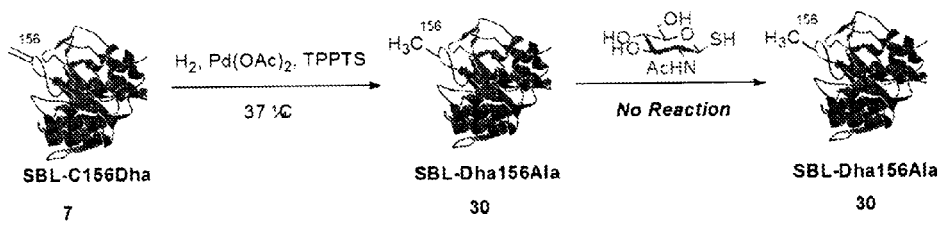
FIG. 12 shows a reaction scheme for conversion of SBL-C156Dha to SBL-Dha156Ala (see Example 21), according to embodiments of the present disclosure.

FIG. 12 shows a reaction scheme for conversion of SBL-C156Dha to SBL-Dha156Ala.

SBL-C156Dha 7 was prepared as described above by the action of MSH on cysteine and purified using a PD10 column, eluting with 50 mM potassium phosphate (pH 8.0). A 200 µL sample of this protein at 0.30 mg/mL (~0.003 µmol) was added to 1.50 mL plastic tube. This solution was stored on ice until needed. A stock catalyst solution was prepared by adding 0.8 mg Pd(OAc)$_2$ (3.6 µmol) and 6.0 mg of TPPTS (10.6 µmol) to a 1.50 mL plastic tube and dissolving in 200 µL of 50 mM sodium phosphate (pH 8.0) with the aid of sonication. This solution is approximately 18 mM in Pd. A 20 µL aliquot of the catalyst solution (~0.3 µmol) was added to the protein solution which was then vortexed to homogenize and sealed with a rubber septa. Hydrogen (1 atm, balloon) was bubbled through the solution for 5 minutes and the reaction incubated in a 37° C. water bath under an $H_2$ atmosphere for 3 hours. After this incubation, a 60 μL aliquot of the reaction mixture was added directly to 1 mg of GlcNAcSH (4.2 μmol; ~5000 eq). The mixture was vortexed to dissolve the thiol and then rotated at room temperature for 30 minutes. LC-MS analysis of the sample showed no addition of GlcNAcSH, indicating that dehydroalanine had been consumed. A mass of 26685 was found which corresponds to the calculated mass of the hydrogenated protein SBL-156Ala (30), 26683.

Example 22

SBL-156-Ethylglycine (SBL-156Etg)

Figure 13:
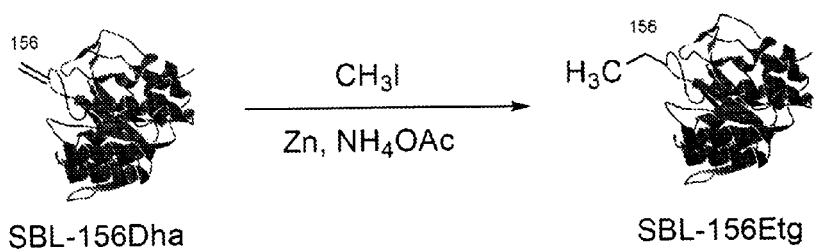
FIG. 13 shows a reaction scheme for the preparation of SBL-156-Ethylglycine (SBL-156Etg) (see Example 22), according to embodiments of the present disclosure.

FIG. 13 shows a reaction scheme for the preparation of SBL-156-Ethylglycine (SBL-156Etg).

A 250 μL aliquot of SBL-156Dha (prepared above; 0.29 mg/mL in pH 6.0 $NH_4OAc$, 500 mM buffer) was thawed and stored on ice until needed. Two doses each of zinc powder (4 mg) and 2 methyliodide (2 μL) were added every five minutes at room temperature. The reaction was shaken vigorously after each addition. The insoluble materials were spun down by centrifugation and the supernatant was analyzed by LC-MS. Approximately 30% conversion was observed so an additional 3 doses of 4 mg of fresh zinc powder and 2 μL of methyliodide were added to the reaction every 5 minutes. The insoluble materials were spun down by centrifugation and the supernatant was analyzed by LC-MS. Full conversion to SBL-156-ethylglycine was observed. 26697 Calculated mass; 26696 found.

The method of Example 22 has also been used to successfully produce modified proteins via addition of the organic iodides ethyl iodide, 1-iodopropane, 1-iodobutane, tert-butyliodide, iodocyclopentane, 2-iodobutane, 2-iodopropane, 2,2-dimethyl-1-iodopropane, 2-methyl-1-iodopropane, 2-iodoethanol, 3-iodopropylamine hydroiodide, 1-iodo-3-acetamidopropane, 1-iodo-3-methylaminopropane, (3-iodopropyl)-dimethylamine hydroiodide, (3-iodopropyl)-trimethylammonium iodide, 4-iodobutyl)amine hydroiodide, (2-iodoethyl)amine hydroiodide, (2-iodoethyl)guanidine hydroiodide, 3-iodopropionic acid, 3-iodopropionamide, 1-iodo-3-fluoropropane, 1-iodo-2,2,2-trifluoroethane and 1-iodo-3,3,3,-trifluoropropane and via the addition of the organic halides chloromethylmethylsulfide and benzylbromide.

Example 23

SBL-PMSF Adduct

Figure 14:
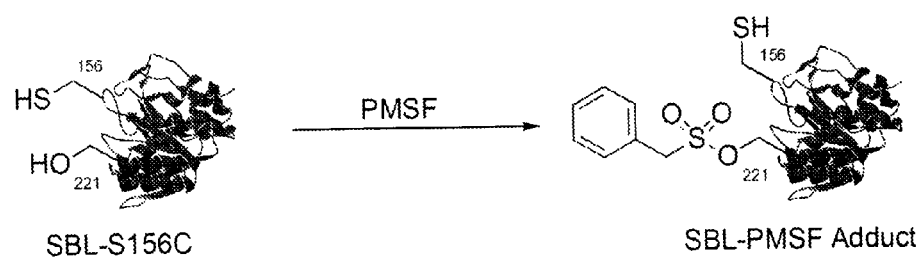
FIG. 14 shows a reaction scheme for the preparation of an SBL-PMSF adduct (see Example 23), according to embodiments of the present disclosure.

FIG. 14 shows a reaction scheme for the preparation of an SBL-PMSF adduct.

A 1.00 mL solution of SBL-S156C was prepared at 1 mg/mL in pH 8.0 sodium phosphate buffer (50 mmol) and stored on ice until needed. A solution of phenylmethanesulfonyl fluoride (PMSF) was prepared by dissolving 4.8 mg (0.028 mmol) in 185 μL MeCN. A 50 μL aliquot of the PMSF solution was added to the protein and the reaction vortexed and rotated at room temperature for 10 minutes. LCMS analysis of the reaction mixture revealed full conversion to the PMSF adduct. (Calculated mass=26869. found 26868). Small molecules were removed using a PD10 column (GE Healthcare) that was equilibrated with the same phosphate buffer. The sample was split into 250 μL aliquots and flash frozen.

Example 24

SBL-221Dha

Figure 15:
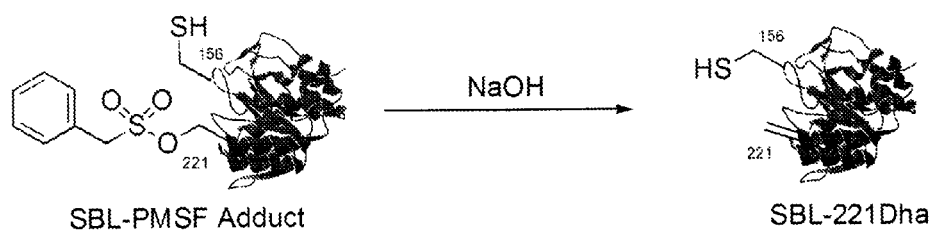
FIG. 15 shows a reaction scheme for the preparation of SBL-221Dha (see Example 24), according to embodiments of the present disclosure.

FIG. 15 shows a reaction scheme for the preparation of SBL-221Dha.

A 250 μL aliquot of the SBL-PMSF adduct prepared above was thawed and stored on ice until needed. 40 μL of 1M NaOH was added to the protein solution at 4° C. The reaction mixture was shaken at 4° C. for 90 minutes and then analyzed directly by LCMS. Full conversion to SBL-221Dha was observed. Calculated Mass=26697. found 26697.

Example 25

SBL-156His$_{iso}$

Figure 16:
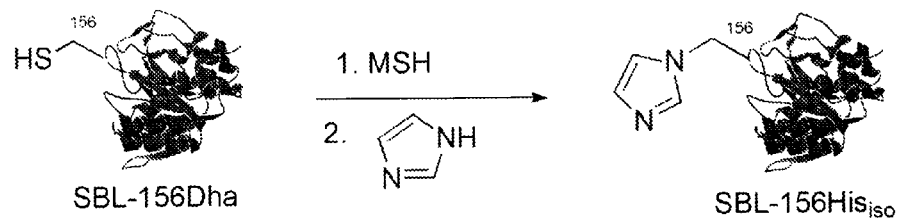
FIG. 16 shows a reaction scheme for the preparation of SBL-156His$_{iso}$ (see Example 25), according to embodiments of the present disclosure.

FIG. 16 shows a reaction scheme for the preparation of SBL-156His$_{iso}$.

A 1.0 mg/mL solution of SBL-S156C was prepared in pH 8.0 sodium phosphate buffer (50 mM) (5 mL total). 1.0 mL of this solution was transferred to each of five 1.5 mL plastic tubes and stored on ice. A solution of MSH (8.3 mg in 500 μL DMF) was prepared and 100 μL of this solution was added to each of the protein samples. All were shaken at 4° C. for 20 minutes. All tubes were then combined and vortexed. LCMS analysis of the mixture revealed full conversion to dehydroalanine (Calculated mass=26681, 26681 found). Imidazole (127 mg) was added to the protein solution and the reaction was shaken at 37° C. for 2 hours. An additional 165 mg of imidazole was added to push the reaction to completion. After 5 hours of total reaction time, LCMS analysis revealed full conversion to isohistidine (Calculated mass=26749, 26749 found) The protein solution was passed through a PD10 column equilibrated with the same buffer (2.5 mL for each of two PD10 columns). This protein solution was used immediately in the next reaction.

Example 26

SBL-156His$_{iso}$ PMSF Adduct

Figure 17:
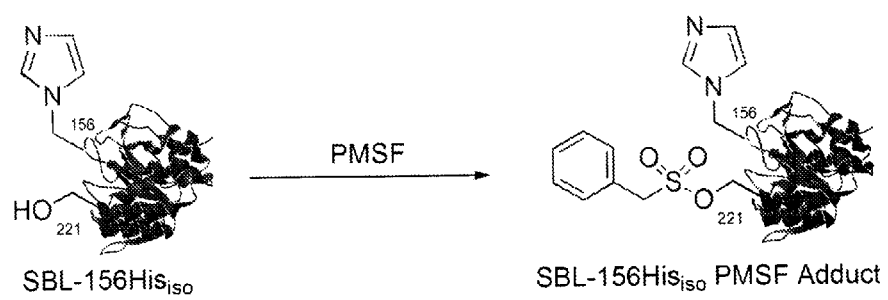
FIG. 17 shows a reaction scheme for the preparation of an SBL-156His$_{iso}$ PMSF adduct (see Example 26), according to embodiments of the present disclosure.

FIG. 17 shows a reaction scheme for the preparation of an SBL-156His$_{iso}$ PMSF adduct.

To 5.0 mL of the SBL-156His$_{iso}$ prepared above (0.71 mg/mL, pH 8.0 sodium phosphate buffer (50 mM)) was added 4.7 mg of PMSF (solution in 200 μL MeCN). The reaction was shaken at room temperature for 20 minutes and then analyzed directly by LCMS. Full conversion to the SBL-156His$_{iso}$ PMSF adduct was observed. Calculated mass=26903. found=26905. Small molecules were removed using PD10 columns equilibrated with the same buffer.

Example 27

SBL-156His$_{iso}$ 221Dha

Figure 18:
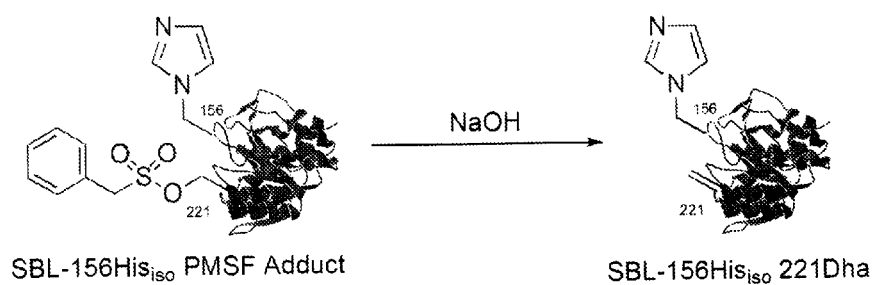
FIG. 18 shows a reaction scheme for the preparation of SBL-156His$_{iso}$ 221Dha (see Example 27), according to embodiments of the present disclosure.

FIG. 18 shows a reaction scheme for the preparation of SBL-156His$_{iso}$ 221Dha.

A 500 μL aliquot of the SBL-156His$_{iso}$ PMSF adduct prepared above (0.51 mg/mL, pH 8.0 sodium phosphate buffer (50 mM)) was added to a plastic tube along with 40 μL of 1.0 M NaOH. The reaction was rotated at 4° C. for two hours. LCMS analysis of the reaction mixture revealed full conversion to SBL-156His$_{iso}$-221Dha. Calculated mass=26731. found 26733.

Recently, biosynthetic incorporation of selenocysteine derivatives into peptides and proteins and conversion to Dha has been reported. These strategies, however, rely on peroxide-induced oxidative elimination that compromises sensitive side chains such as methionine (Met). Dehydroalanine (Dha) is a unique chemical handle for such modifications and the present methods allow access to Dha without undesirable alteration to the remainder of a peptide or protein.

The inventive method avoids the need to ligate a desired peptide at a point where there should be a naturally occurring cysteine thereby expanding the potential scission points for retrosynthesis of large peptides and giving the researcher more options when choosing potential ligation points when synthetically constructing a polypeptide. The methods also allows the use of native chemical ligation in the synthesis of peptides that do not contain cysteine.

Routes to various naturally occurring amino acid side chains are shown in the following figure.

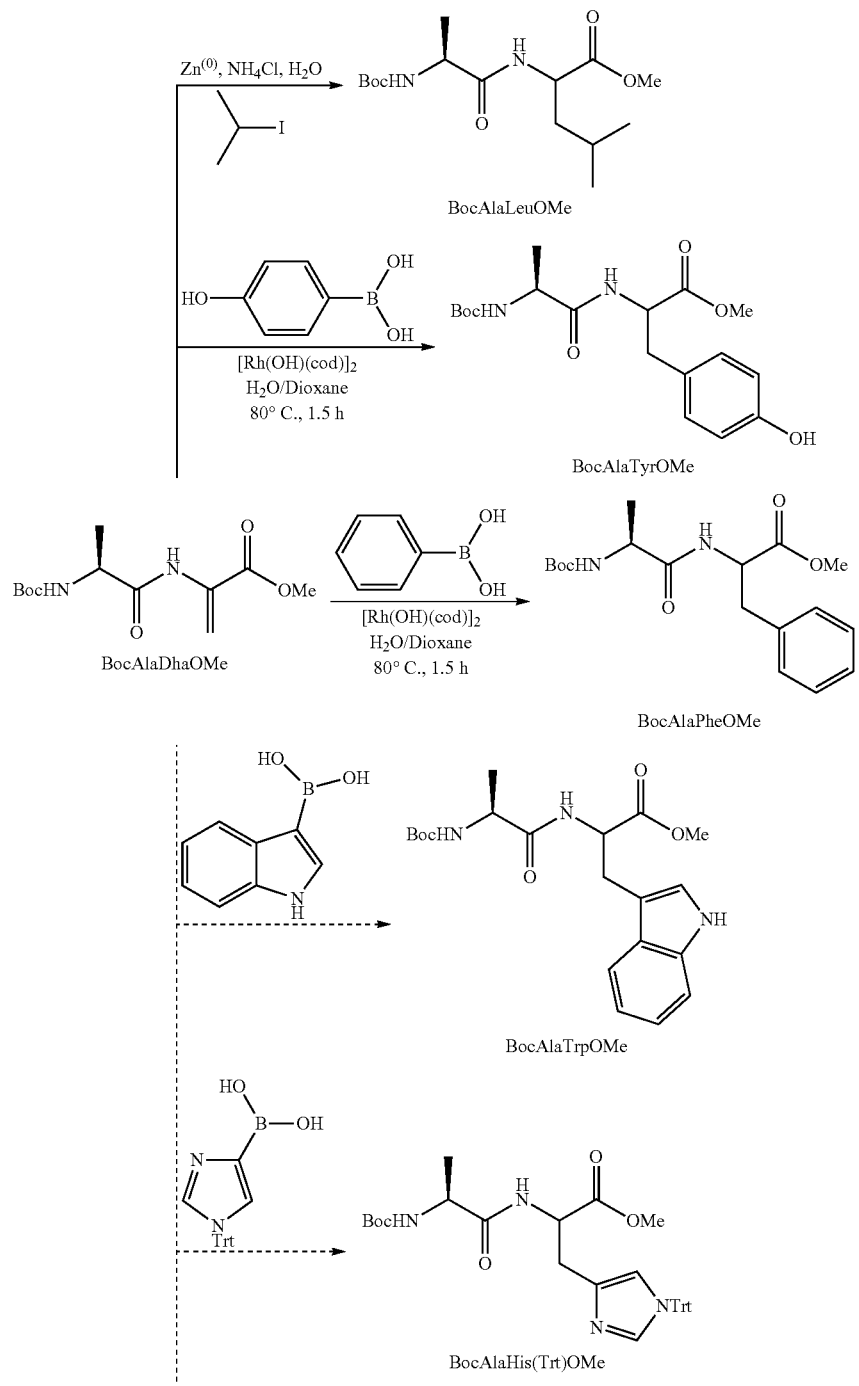

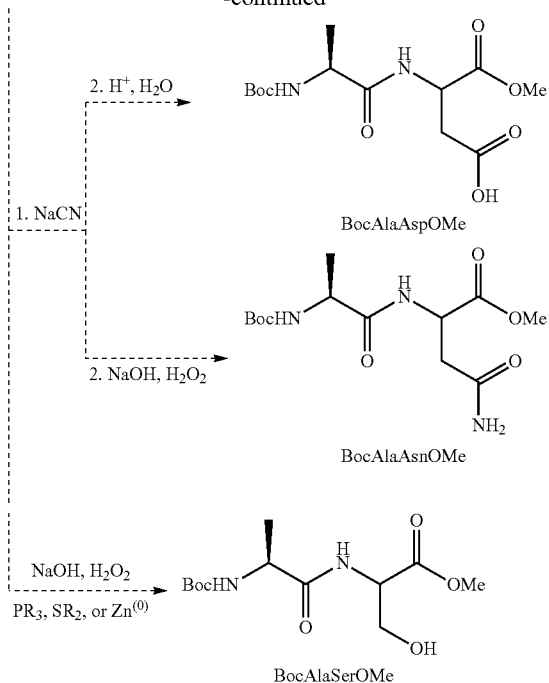

The invention claimed is:

1. A method for converting an unmodified cysteine residue of a peptide or protein to a dehydroalanine residue, the method comprising:

reacting an unmodified cysteine residue of the peptide or protein with a sulfonylhydroxylamine of formula:

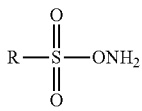

wherein R is an electron withdrawing group, and wherein the method is performed at a pH of between 6 and 10, to convert the unmodified cysteine residue to a dehydroalanine residue.

2. The method of claim 1 wherein the sulfonylhydroxylamine is O-mesitylenesulfonylhydroxylamine.

3. The method of claim 1 wherein said reacting the unmodified cysteine residue with the sulfonylhydroxylamine takes place in a solution or suspension in a polar aprotic solvent.

4. The method of claim 3 wherein the polar aprotic solvent is dimethylformamide (DMF).

5. The method of claim 1 wherein said reacting the unmodified cysteine residue with sulfonylhydroxylamine takes place in the presence of a base.

6. The method of claim 5 wherein the base comprises a potassium carbonate or a phosphate buffer.

7. The method of claim 1 comprising a subsequent step of reacting the carbon-carbon double bond of the dehydroalanine residue.

8. The method of claim 7 wherein the step of reacting the carbon-carbon double bond is stereoselective.

9. The method of claim 7 wherein the carbon-carbon double bond of the dehydroalanine residue is reacted with a thiol to form a thioether derivatized peptide or protein.

10. The method of claim 7 wherein the carbon-carbon double bond of the dehydroalanine residue is reacted with an organoborate.

11. The method of claim 7 wherein the carbon-carbon double bond of the dehydroalanine residue is reacted with a organohalide in the presence of elemental zinc.

12. A method for producing a peptide or protein comprising the steps of:

a) joining two polypeptides by native chemical ligation, thereby forming a joined polypeptide; and b) contacting the joined polypeptide with a sulfonylhydroxylamine to achieve conversion of an unmodified cysteine residue of the polypeptide to a dehydroalanine residue, wherein the sulfonylhydroxylamine has the formula:

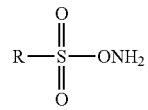

and wherein R is an electron withdrawing group, and wherein the method is performed at a pH of between 6 and 10.

13. The method of claim 12 wherein the unmodified cysteine residue is located at the site of native chemical ligation.

14. A method of converting an unmodified cysteine residue of a peptide or protein to a dehydroalanine residue, the method comprising:

reacting an unmodified cysteine residue of the peptide or protein with O-mesitylenesulfonylhydroxylamine, wherein the step of contacting takes place in dimethylformamide, and wherein the method is performed at a pH between 6 and 10, to convert the unmodified cysteine residue to a dehydroalanine residue.

15. The method of claim 1, further comprising reversibly denaturing the peptide or protein before said reacting.

* * * * *